(12) United States Patent
Liu et al.

(10) Patent No.: US 9,857,344 B2
(45) Date of Patent: Jan. 2, 2018

(54) GAS DETECTION SENSOR, DISPLAY PANEL, AND DISPLAY DEVICE

(71) Applicant: BOE TECHNOLOGY GROUP CO., LTD., Beijing (CN)

(72) Inventors: Xiaodi Liu, Beijing (CN); Cuili Gai, Beijing (CN); Fengjuan Liu, Beijing (CN); Gang Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 163 days.

(21) Appl. No.: 14/574,841

(22) Filed: Dec. 18, 2014

(65) Prior Publication Data
US 2016/0011158 A1      Jan. 14, 2016

(30) Foreign Application Priority Data

Jul. 11, 2014    (CN) .......................... 2014 1 0332109

(51) Int. Cl.
*G01N 33/00*      (2006.01)
*H01L 29/22*     (2006.01)
(Continued)

(52) U.S. Cl.
CPC ..... *G01N 33/0027* (2013.01); *G01N 33/0062* (2013.01); *H01L 29/22* (2013.01); *H01L 29/26* (2013.01); *H01L 29/786* (2013.01)

(58) Field of Classification Search
None
See application file for complete search history.

(56) References Cited

U.S. PATENT DOCUMENTS 4,621,182 A  *  11/1986  Driggers .................. H05B 3/46
                                                                219/523
5,601,693 A  *   2/1997  Davies .................... G01N 27/16
                                                                204/400
(Continued)

FOREIGN PATENT DOCUMENTS

CN     102778479 A    11/2012
CN     103499906 A     1/2014
(Continued)

OTHER PUBLICATIONS

Second Office Action for Chinese Patent Application No. 201410332109.5, dated Aug. 29, 2016, 12 pages.
(Continued)

*Primary Examiner* — Paul West
*Assistant Examiner* — Mark A Shabman
(74) *Attorney, Agent, or Firm* — Westerman, Champlin & Koehler, P.A.

(57) ABSTRACT

Embodiments of the present invention provide a gas detection sensor, a display panel, and a display device. The gas detection sensor comprises: a gas sensitive part; two detection electrodes electrically connected with each other through the gas sensitive part; and a protective layer enclosing the gas sensitive part and the detection electrodes. When one of the detection electrodes is applied with a detecting signal, the detecting signal is output from the other detection electrode after being modulated by the gas sensitive part, and a voltage signal output by the other detection electrode is related to a nature of the outside air to which the gas sensitive part is exposed, thereby a detection on air quality may be achieved through detecting the voltage signal output from the other detection electrode, such that a simply structured and portable gas detection sensor can be realized.

13 Claims, 7 Drawing Sheets

(51) Int. Cl.
    *H01L 29/786*     (2006.01)
    *H01L 29/26*     (2006.01)

(56) References Cited

U.S. PATENT DOCUMENTS

| | | | | |
|---|---|---|---|---|
| 5,993,624 | A * | 11/1999 | Matsubara | G01N 27/12 204/421 |
| 6,555,159 | B2 * | 4/2003 | Clyde | C23C 4/18 427/126.3 |
| 8,592,875 | B2 | 11/2013 | Wilbertz et al. | |
| 2002/0100688 | A1 * | 8/2002 | Detwiler | G01N 27/4071 204/431 |
| 2006/0065526 | A1 * | 3/2006 | Ono | G01N 27/4075 204/426 |
| 2007/0272922 | A1 * | 11/2007 | Kim | H01L 29/7869 257/43 |
| 2008/0296568 | A1 * | 12/2008 | Ryu | H01L 21/02554 257/43 |
| 2009/0159446 | A1 * | 6/2009 | Cui | G01N 27/125 204/424 |
| 2011/0031537 | A1 | 2/2011 | Widenmeyer et al. | |
| 2011/0303953 | A1 * | 12/2011 | Kamata | H01L 27/12 257/253 |
| 2012/0180563 | A1 * | 7/2012 | Wang | G01F 1/692 73/204.26 |

FOREIGN PATENT DOCUMENTS

| | | |
|---|---|---|
| EP | 2 594 928 A2 | 5/2013 |
| WO | 2009/095285 A1 | 8/2009 |

OTHER PUBLICATIONS

First Office Action, including Search Report, for Chinese Patent Application No. 201410332109.5, dated Mar. 10, 2016, 7 pages.
Rejection Decision for Chinese Patent Application No. 201410332109.5, dated Nov. 4, 2016, 12 pages.
Reexamination Notification from Chinese Patent Application No. 201410332109.5, dated Jun. 15, 2017, 15 pages.

\* cited by examiner

GAS DETECTION SENSOR, DISPLAY PANEL, AND DISPLAY DEVICE

CROSS-REFERENCE TO RELATED APPLICATION

This application claims the benefit of Chinese Patent Application No. 201410332109.5 filed on Jul. 11, 2014 in the State Intellectual Property Office of China, the whole disclosure of which is incorporated herein by reference.

BACKGROUND OF THE INVENTION

Field of the Invention

The embodiments of the present invention relates to the field of semiconductor technology, and particularly to a gas detection sensor, a display panel, and a display device.

Description of the Related Art

In a daily life environment, or in a new environment where people are on trip or on business, air quality, for example, hazardous gas or flammable gas components in the air, will directly affect people's health and safety. Therefore, people have paid more and more attention to air quality where they live.

Recently, environmental air quality is detected through gas detection devices. However, existing gas detection devices are only suitable for detecting air quality in a fixed place, and not used in various places where people are involved due to their complicated structures and large volumes. Therefore, it is necessary to provide a gas detection device which is portable and simple in structure such that people can know environmental air quality at any moment and anywhere.

SUMMARY OF THE INVENTION

Embodiments of the present invention provide a gas detection sensor, which is simple in structure and portable. Embodiments of the present invention further provide a display panel comprising the gas detection sensor and a display device comprising the display panel.

One embodiment of the present invention provides a gas detection sensor, comprising: a gas sensitive part; two detection electrodes electrically connected with each other through the gas sensitive part; and a protective layer enclosing the gas sensitive part and the detection electrodes, wherein the protective layer has an opening region through which the gas sensitive part is exposed to an outside air;

the gas sensitive part is formed by oxygen containing compound semiconductor material;

wherein when one of the detection electrodes is applied with a detecting signal, the detecting signal is output from the other detection electrode after being modulated by the gas sensitive part, and a voltage signal output by the other detection electrode is related to a nature of the outside air to which the gas sensitive part is exposed.

According to one embodiment of the present invention, in order to improve sensitivity of the gas detection sensor, the above gas detection sensor further comprises a heating electrode electrically insulated from the gas sensitive part and configured to convert electrical energy to heat energy to heat the gas sensitive part.

In order to facilitate the implementation of the present invention, the gas detection sensor further comprises a heating electrode wire electrically connected with the heating electrode for providing electrical energy to the heating electrode.

According to one embodiment of the present invention, in order to decrease power consumption on the heating electrode wire, the gas detection sensor further comprises a connecting portion connected in parallel with the heating electrode wire and configured to decrease the resistance of the heating electrode wire.

In order to facilitate the implementation of the present invention, the oxygen containing compound semiconductor material may comprise any one of ZnON, ITZO, ZTO, ZIO, IGO, IGZO, AZTO, or any combination thereof.

One embodiment of the present invention provides a display panel, comprising: an array substrate; an opposing substrate disposed opposite to the array substrate; an adhesive frame hermetically connecting the array substrate and the opposing substrate so as to form a sealed space; and at least a gas detection sensor according to any one of the embodiments of the present invention, wherein the gas detection sensor is disposed on the array substrate and/or the opposing substrate outside of the adhesive frame.

In order to simplify production process and reduce production cost, according to one embodiment, in the above display panel, when the gas detection sensor is disposed on the array substrate, the gas sensitive part of the gas detection sensor and an active layer of a thin film transistor in the array substrate are located in the same layer and formed from the same material.

In order to simplify production process and reduce production cost, according to one embodiment, in the above display panel, the gas sensitive part of the gas detection sensor is located in the same layer as source and drain electrodes or a gate electrode of the thin film transistor in the array substrate and formed from the same material as source and drain electrodes or a gate electrode of the thin film transistor.

According to one embodiment, to simplify production process and reduce production cost, in the above display panel, the gas detection sensor comprises a heating electrode, the heating electrode is located underneath the gas sensitive part, and when the gate electrode of the thin film transistor in the array substrate is located underneath the active layer, the heating electrode and the gate electrode are located in the same layer and formed from the same material; or when the source and drain electrodes of the thin film transistor in the array substrate are located underneath the active layer, the heating electrode and the source and drain electrodes are located in the same layer and formed from the same material.

In order to simplify production process and reduce production cost, according to one embodiment, in the above display panel, when the gate electrode of the thin film transistor in the array substrate is located underneath the active layer, and the heating electrode and the gate electrode are located in the same layer and formed from the same material, and the gas detection sensor comprises a heating electrode wire and a connecting portion:

the heating electrode wire and the heating electrode of the gas detection sensor are located in the same layer and formed from the same material; and the connecting portion and the source and drain electrodes of the thin film transistor are located in the same layer and formed from the same material, and the connecting portion is electrically connected to the heating electrode wire through a via hole.

One embodiment of the present invention provides a display device, comprising the display panel according to any one of the embodiments above.

BRIEF DESCRIPTION OF THE DRAWINGS

The above and other features of the present invention will become more apparent by describing in detail exemplary embodiments thereof with reference to the accompanying drawings, in which.

DETAILED DESCRIPTION OF PREFERRED EMBODIMENTS OF THE INVENTION

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art. Further, sizes or shapes shown in the drawings only intend to explicitly describe the present invention, and do not intend to reflect practical proportions.

Figure 1:
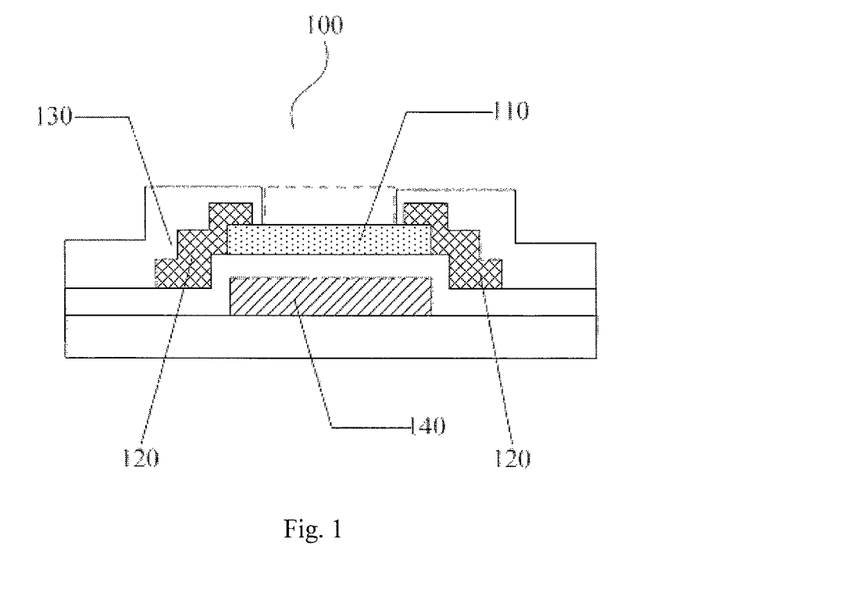
FIG. 1 is an illustrative cross-section view of a gas detection sensor according to one embodiment of the present invention.
Figure 2:
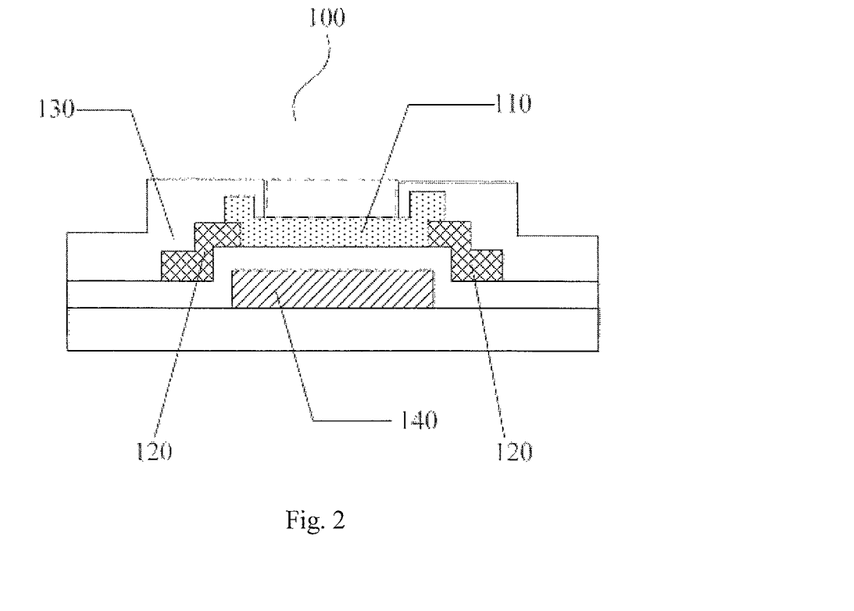
FIG. 2 is an illustrative cross-section view of a gas detection sensor according to another embodiment of the present invention taken along a line A-A of FIG. 3.
Figure 3:
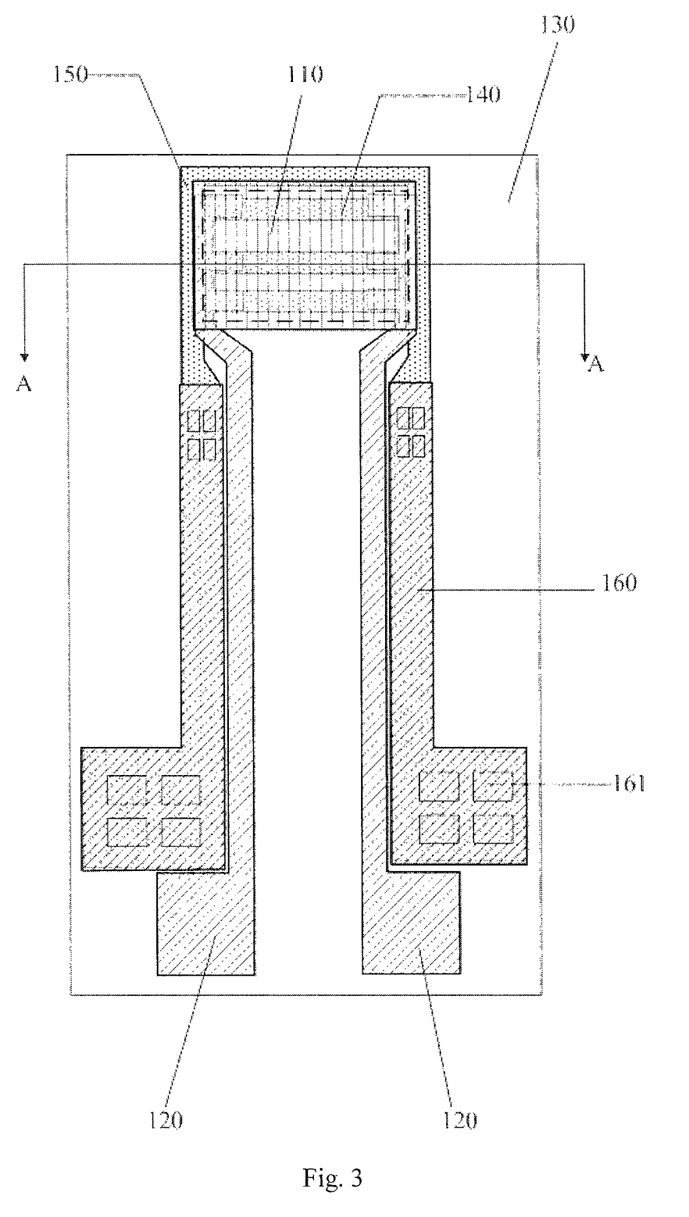
FIG. 3 is a top view of the gas detection sensor of FIG. 2.

FIG. 1 is an illustrative cross-section view of a gas detection sensor according to one embodiment of the present invention. FIG. 2 is an illustrative cross-section view of a gas detection sensor according to another embodiment of the present invention taken along a line A-A of FIG. 3, and FIG. 3 is a top view of the gas detection sensor of FIG. 2. As shown in FIGS. 1-3, a gas detection sensor 100 comprises a gas sensitive part 110, two detection electrodes 120 connected with each other through the gas sensitive part and a protective layer 130 enclosing the gas sensitive part 110 and the detection electrodes 120, wherein the protective layer 130 has an opening region (indicated by the dashed line in FIG. 1) through which the gas sensitive part 110 is exposed to an outside air. The gas sensitive part 110 is formed from an oxygen containing compound semiconductor material.

When one detection electrode 120 is applied with a detecting signal, the detecting signal is output from the other detection electrode 120 after being modulated by the gas sensitive part 110, and a voltage signal output by the other detection electrode 120 is related to a nature of the outside air to which the gas sensitive part 110 is exposed.

The gas detection sensor according to the present invention comprises a gas sensitive part, two detection electrodes connected through the gas sensitive part, and a protective layer enclosing the gas sensitive part and the detection electrodes. When one detection electrode is applied with a detecting signal, the detecting signal is output from the other detection electrode after being modulated by the gas sensitive part, and a voltage signal output by the other detection electrode is related to a nature of the outside air to which the gas sensitive part is exposed. Therefore, by detecting the value of the voltage signal output from the other detection electrode, air quality can be detected. Therefore, a simply structured and portable gas detection sensor can be realized.

For example, if the material of the gas sensitive part is an electron conduction type material, then when the outside air to which the gas sensitive part is exposed is a reductive gas, the voltage of the detecting signal output from the other detection electrode will reduce; when the outside air to which the gas sensitive part is exposed is an oxidative gas, the voltage of the detecting signal output from the other detection electrode will increase. In contrast, if the material of the gas sensitive part is a hole conduction type material, then when the outside air to which the gas sensitive part is exposed is a reductive gas, the voltage of the detecting signal output from the other detection electrode will increase; when the outside air to which the gas sensitive part is exposed is an oxidative gas, the voltage of the detecting signal output from the other detection electrode will reduce. Therefore, when a detecting signal is applied to one detection electrode, a nature of the outside air may be determined based on a magnitude of the voltage output from another detection electrode, thereby air quality or the like can be detected.

In the gas detection sensor according to embodiments of the present invention, the oxygen containing compound semiconductor material may comprise any one of ZnON, ITZO, ZTO, ZIO, IGO, IGZO, AZTO, or any combination thereof, which is not limited herein.

Furthermore, in the gas detection sensor according to embodiments of the present invention, the detection electrodes may be made of conductive metal or alloy, which is not limited herein. Specifically, the material of the detection electrodes may be Mo, Al, Cu, Al/Nd alloy, Al/Nd/Mo alloy, Mo/Al/Nd/Mo alloy, Au/Ti alloy, and the like.

In order to improve sensitivity of the gas detection sensor, as shown in FIGS. 1 to 3, the gas detection sensor may further comprise a heating electrode 140, which is electrically insulated from the gas sensitive part and is configured to convert electrical energy to heat energy to heat the gas sensitive part 110. By being heated by the heating electrode 140, the gas sensitive part 110 can have a temperature satisfying a temperature condition required for generating reaction with the outside air, and therefore detection sensitivity of the gas detection sensor is improved.

Furthermore, in the gas detection sensor according to embodiments of the present invention, the heating electrodes may be made from a conductive metal or an alloy, which is not limited herein. Specifically, the material of the detection electrodes may be made from Mo, Al, Cu, Al/Nd alloy, Al/Nd/Mo alloy, Mo/Al/Nd/Mo alloy, Au/Ti alloy, or the like.

As shown in FIG. 3, the gas detection sensor may further comprise a heating electrode wire 150 electrically connected with the heating electrode 140 for providing electrical energy to the heating electrode 140.

Furthermore, the material of the heating electrode wire may be the same or not the same as that of the heating electrode, which is not limited herein.

In the gas detection sensor according to embodiments of the present invention, since the heating electrode is used to convert electrical energy to heat energy, the heating electrode needs a high power. In order to provide a high power to the heating electrode, a power on the heating electrode wire should be high accordingly. However, a high power on the heating electrode wire leads to unnecessary power consumption, and will also affect a heating efficiency of the heating electrode. Therefore, in order to improve heating efficiency of the heating electrode and reduce power consumption on the heating electrode wire, as shown in FIG. 3, the gas detection sensor 100 further comprises a connecting portion 160, which is connected in parallel with the heating electrode wire 150 and configured to decrease the resistance of the heating electrode wire 150.

Specifically, when the connecting portion 160 does not lie in the same layer as the heating electrode wire 150, the connecting portion 160 may be electrically connected to the heating electrode wire 150 through a via hole 161, as shown in FIG. 3.

Further, in the gas detection sensor according to embodiments of the present invention, when a voltage output from a detection electrode changes, a detection and an analysis of components of air to which the gas sensitive part 110 is exposed, and of the concentrations and types thereof are performed by using a suitable algorithm, such as a neural network algorithm, and a display alarm is thereafter performed.

Figure 4:
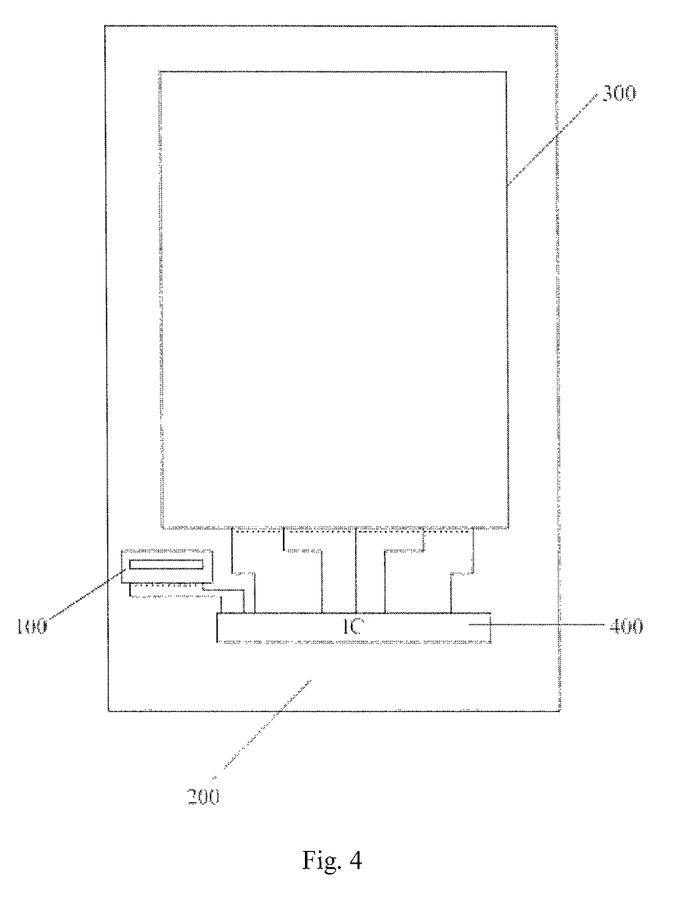
FIG. 4 is an illustrative structural view of a display panel according to one embodiment of the present invention.

FIG. 4 shows a display panel according to one embodiment of the present invention. As shown in FIG. 4, the display panel comprises an array substrate 200, an opposing substrate (not shown in FIG. 4) disposed opposite to the array substrate 200, and an adhesive frame 300 hermetically connecting the array substrate 200 and the opposing substrate to form a sealed space. The display panel further comprises at least one gas detection sensor 100 according to the above embodiments of the present invention, the gas detection sensor 100 being disposed on the array substrate 200 and/or the opposing substrate and located outside the sealed space.

With a display panel according to the embodiment of the present invention which comprises a gas detection sensor, people may detect air quality in any place where he is by a portable display panel without specially carrying with a gas detection device, or detect air quality in daily life environment by the display panel.

Specifically, in the above display panel, when the gas detection sensor is disposed on the array substrate, as shown in FIG. 4, the gas detection sensor 100 may utilize the common drive integrated circuit (Drive IC) 400 with the display panel. Of course, a separate Drive IC may be provided for the gas detection sensor, which is not limited herein.

Figure 5:
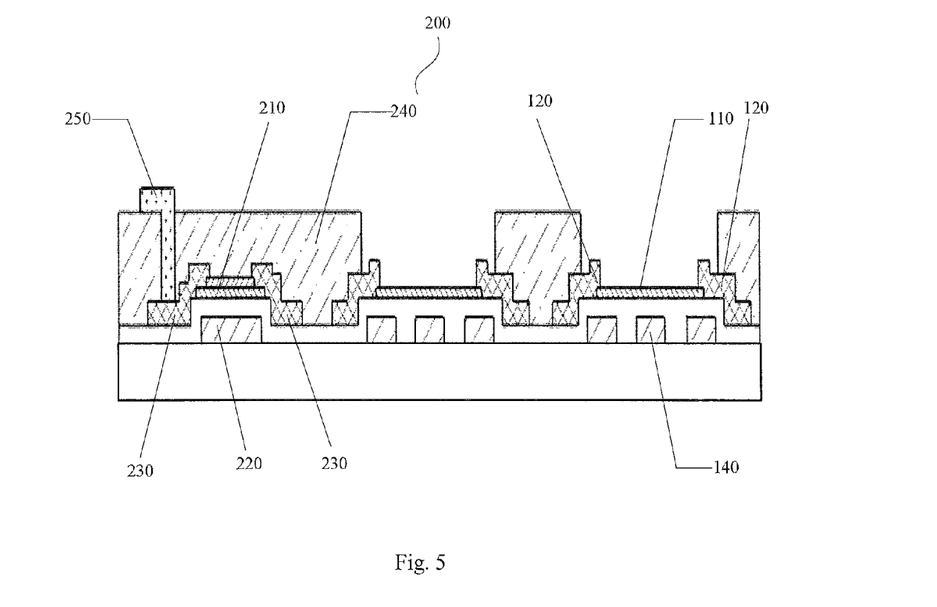
FIG. 5 is an illustrative structural view of an array substrate according to one embodiment of the present invention.

In order to simplify production process and reduce production cost, in the display panel according to an embodiment of the present invention, when the gas detection sensor is disposed on the array substrate, as shown in FIG. 5, a gas sensitive part 110 of the gas detection sensor and an active layer 210 of a thin film transistor (TFT) in the array substrate 200 may be located in the same layer and formed from the same material. With such a configuration, no additional manufacturing processes are needed for manufacturing the gas detection sensor; instead, the gas detection sensor can be made during the production of the array substrate by changing a pattern of each film layer, thereby production cost is reduced and production efficiency is improved.

Further, when the gas detection sensor is provided with a heating electrode 140, as shown in FIG. 5, the heating electrode 140 is located underneath the gas sensitive part 110, thereby a contact between the gas sensitive part 110 and outside air can be ensured.

In order to simplify production process and reduce production cost, in the display panel according to an embodiment of the present invention, as shown in FIG. 5, the gas detection electrode 120 of the gas detection sensor and the active layer 210 of the thin film transistor in the array substrate are located in the same layer and formed from the same material. Or, although not shown, the gas detection electrode 120 of the gas detection sensor and a gate electrode 220 of the thin film transistor are located in the same layer and formed from the same material. With such a configuration, no additional manufacturing processes are needed for manufacturing the detection electrode; by changing a pattern of each film layer, the detection electrode can be made during the production of the array substrate, thereby production cost is reduced and production efficiency is improved.

Further, in order to simplify production process and reduce production cost, in the display panel according to an embodiment of the present invention, as shown in FIG. 5, when the gate electrode 220 of the thin film transistor in the array substrate 200 is located underneath the active layer 210, the heating electrode 140 and the gate electrode 220 are located in the same layer and formed from the same material. Or, although not shown, when the source and drain electrodes 230 of the thin film transistor in the array substrate are located underneath the active layer, the heating electrode 140 and the source and drain electrodes 230 are located in the same layer and formed from the same material.

In order to simplify production process and reduce production cost, in the display panel according to an embodiment of the present invention, as shown in FIG. 5, when the gate electrode 220 of the thin film transistor in the array substrate 200 is located underneath the active layer 210, the heating electrode 140 and the gate electrode 220 are located in the same layer and formed from the same material, and the gas detection sensor comprises the heating electrode wire and the connecting portion (not shown in FIG. 5):

the heating electrode wire and the heating electrode of the gas detection sensor are located in the same layer and formed from the same material;

the connecting portion and the source and drain electrodes of the TFT are located in the same layer and formed from the same material; and the connecting portion is electrically connected to the heating electrode wire through a via hole.

Figure 6:
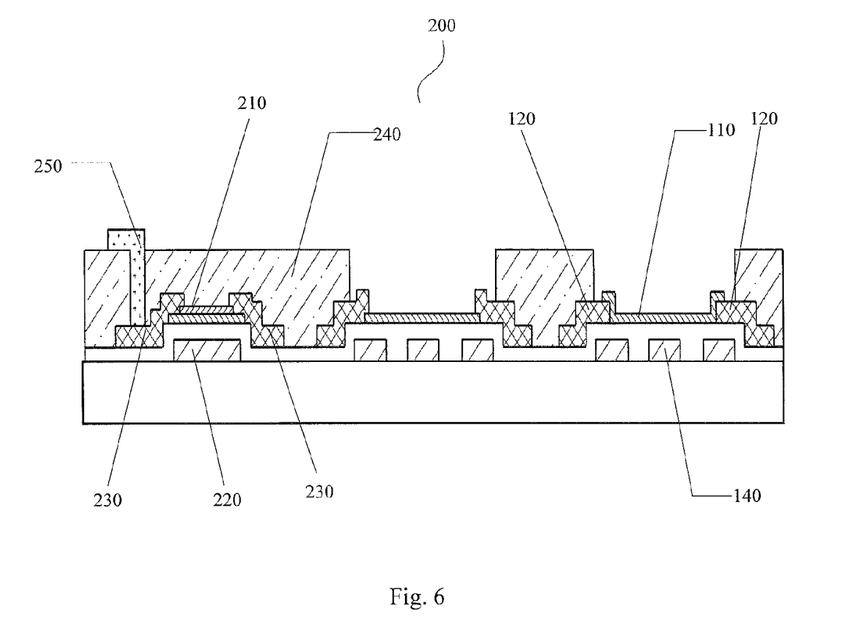
FIG. 6 is an illustrative structural view of an array substrate according to another embodiment of the present invention.

Furthermore, in a display panel according to one embodiment of the present invention, a gas sensitive part of a gas detection sensor and an active layer of a TFT in the array substrate may not be located in the same layer. Specifically, as shown in FIG. 6, a heating electrode 140 of the gas detection sensor and a gate electrode 220 of a TFT in the array substrate 200 are located in the same layer and formed from the same material, a heating electrode wire 150 and the heating electrode 140 are located in the same layer and formed from the same material (not shown in FIG. 6), a detection electrode 120 and source and drain electrodes 230 of the TFT are located in the same layer and formed from the same material. In the TFT, an active layer 210 is located between the source and drain electrodes 230 and the gate electrode 220. In the gas detection sensor, a gas sensitive part 110 is located above a detection electrode 120.

Furthermore, in the above display panel according to an embodiment of the present invention, as shown in FIGS. 5 and 6, the array substrate 200 may further comprise a passive layer 240 located above the TFT and the gas detection sensor, and a pixel electrode 250 located above the passive layer 240, the pixel electrode 250 being connected to the source and drain electrodes of the TFT through a via hole penetrating through the passive layer 240. The structures of the TFT and the pixel electrode 250 electrically connected to the TFT belong to prior art, a detailed description thereof is omitted herein.

Specifically, taking the array substrate shown in FIG. 5 as an example, production processes of an array substrate comprising a gas detection sensor will be described in detail.

Specifically, a process for producing an array substrate comprises the following steps.

Figure 7A:
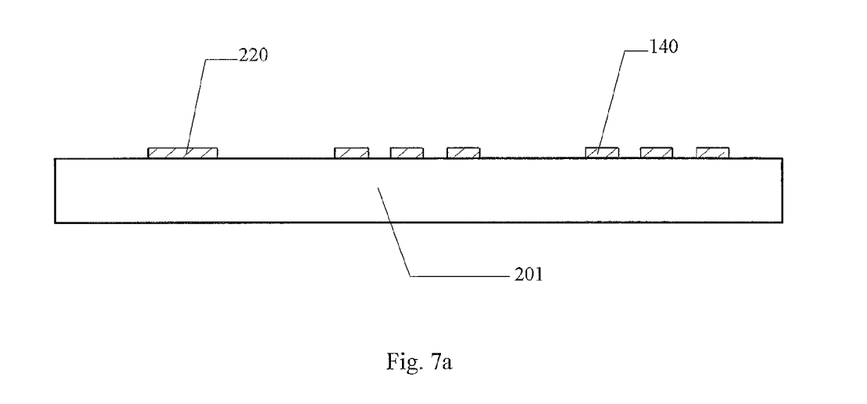
FIGS. 7a to 7e are illustrative structural views showing a process of producing the array substrate of FIG. 5.

(1) Forming patterns of a gate electrode 220 and a heating electrode 140 on an underlying substrate 201 through one-step patterning process, as shown in FIG. 7a.

Specifically, in practice, the underlying substrate may be formed from glass, polyimide, silicon, or the like, which is not limited herein. A film formed from metal or alloy such as Mo, Al, Cu, Al/Nd alloy, Al/Nd/Mo alloy, Mo/Al/Nd/Mo alloy, Au/Ti alloy, or the like is deposited through sputtering, then the patterns of the gate electrode 220 and the heating electrode 140 are formed through one-step patterning process.

Furthermore, in practice, a pattern of a heating electrode wire may be formed at the same time as forming the patterns of the gate electrode 220 and the heating electrode 140 through one-step patterning process.

Figure 7B:
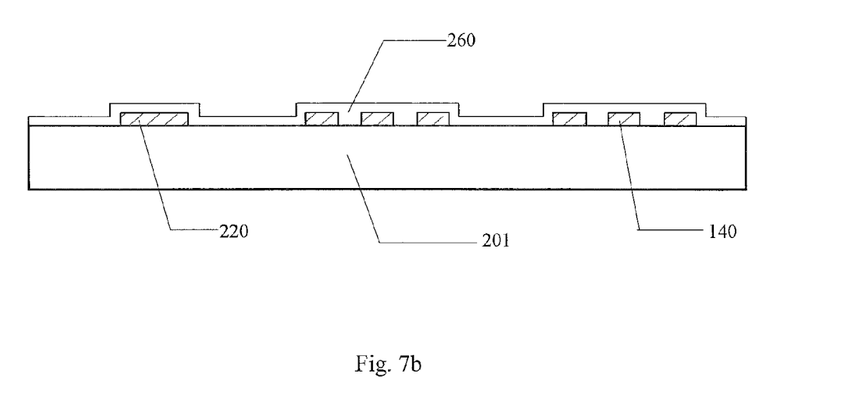

(2) Depositing a gate insulation layer 260 above the gate electrode 220 and the heating electrode 140, as shown in FIG. 7b.

Specifically, in practice, one or more gate insulation layers formed from $SiO_x$, $SN_x$, $Al_2O_3$, $HfO_2$, $ZrO_2$, $TiO_2$, $Y2O_3$, $La_2O_3$, $Ta_2O_5$, or the like are formed through Atmospheric Pressure CVD, Low Pressure CVD, Plasma Assisted CVD, spluttering, or the like.

Figure 7C:
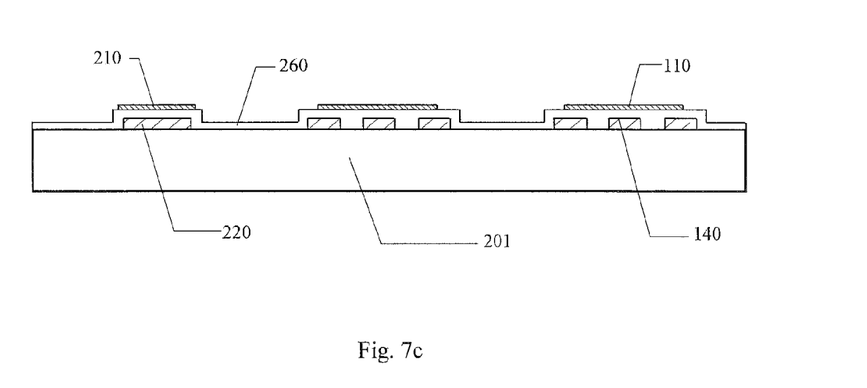

(3) Forming patterns of an active layer 210 and a gas sensitive part 110 above the gate insulation layer 260 through one-step patterning process, as shown in FIG. 7c.

Specifically, in practice, the active layer and the gas sensitive part may be formed from any one of ZnON, ITZO, ZTO, ZIO, IGO, IGZO, AZTO, or any combination thereof. Furthermore, a film layer of the active layer and the gas sensitive part may be formed through spluttering, Sol-Gel processing, vacuum evaporating, spray coating, ink jet printing, or the like, and then the patterns of the active layer and the gas sensitive part may be formed in the film layer through one-step patterning process.

Figure 7D:
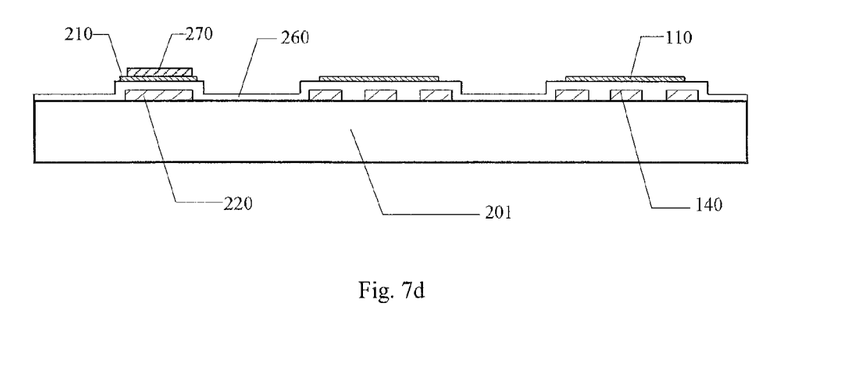

(4) Forming an etch-resist layer 270 above the active layer 210, as shown in FIG. 7d.

Specifically, in practice, the etch-resist layer of the TFT formed from one or more of $SiO_x$, $SN_x$, $Al_2O_3$ and the like is formed through Atmospheric Pressure CVD, Low Pressure CVD, Plasma Assisted CVD, spluttering, thermal growth or the like.

Figure 7E:
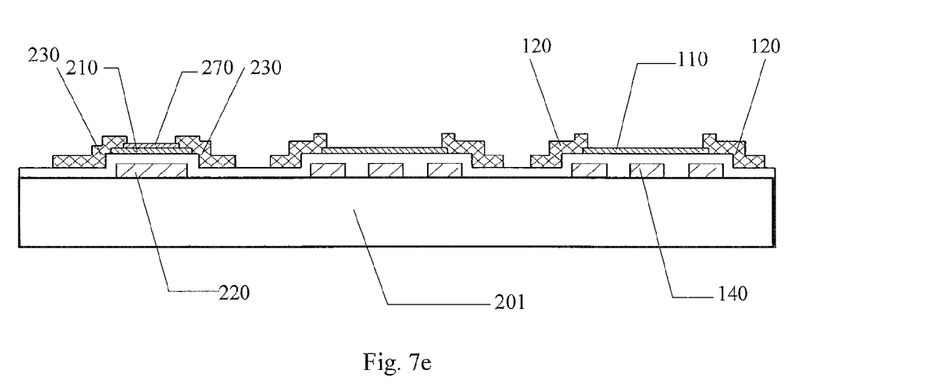

(5) Forming patterns of source and drain electrodes 230 and a detection electrode 120 through one-step patterning process, as shown in FIG. 7e.

Specifically, in practice, the source and drain electrodes and the detection electrode may be formed from metal or alloy such as Mo, Al, Cu, Al/Nd alloy, Al/Nd/Mo alloy, Mo/Al/Nd/Mo alloy, Au/Ti alloy, or the like.

Further, specifically, a pattern of a connecting portion may be formed at the same time as forming the source and drain electrodes and the detection electrode through one-step patterning process, and the connection portion is electrically connected to the heating electrode wire through a via hole penetrating through the gate insulation layer.

(6) Forming a passive layer 240 above the source and drain electrodes 230 and the detection electrode 120, and forming a pixel electrode 250 on the passive layer 240, as shown in FIG. 5.

Specifically, in practice, one or more films formed from $SiO_x$, $SiN_x$, and $SiO_xN_y$ are formed through thermal growth, Atmospheric Pressure CVD, Low Pressure CVD, Plasma Assisted CVD, spluttering, or the like, and a via hole which connects the pixel electrode with the source and drain electrodes and an opening region through which the gas sensitive part contacts outside air are formed in the passive layer through etching.

Further, in order to eliminate defects in the material of the gas sensitive part and to decrease a resistance of the pixel electrode, a step (7) of annealing the above array substrate in vacuum, nitrogen, or oxygen atmosphere may be further added behind the step (6).

Specifically, in practice, a temperature of the annealing is maintained within a range from 120° C. to 450° C., and a period of the annealing is preferably within a range from 0.5 hour to 2 hours.

Please note that the above step (1) to step (7) is just to explain a manufacturing method based on, for example, the array substrate shown in FIG. 5. The manufacturing method may vary depending on the structure of the gas detection sensor, which is not limited herein.

Specifically, the display panel provided according to embodiments of the present invention may be a LCD panel, or an OLED panel, which is not limited herein.

Based on the same inventive concept, one embodiment of the present invention further provides a display device comprising the above display panel according to one embodiment of the present invention. The display device may be a product having a display function or a part of a product, such as a mobile phone, a tablet, a TV set, a display, a notebook computer, a digital frame, a navigator, or the like. Embodiments of the display device may refer to the above embodiments concerning the display panel, which will be omitted for the sake of simplicity.

Embodiments of the present invention provide a gas detection sensor, a display panel, and a display device. The gas detection sensor comprises: a gas sensitive part; two detection electrodes electrically connected with each other through the gas sensitive part; and a protective layer enclosing the gas sensitive part and the detection electrodes. When one of the detection electrodes is applied with a detecting signal, the detecting signal is output from the other detection electrode after being modulated by the gas sensitive part, and a voltage signal output by the other detection electrode is related to a nature of the outside air to which the gas sensitive part is exposed, thereby a detection on air quality may be achieved through detecting the voltage signal output from the other detection electrode, such that a simply structured and portable gas detection sensor can be realized.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A gas detection sensor, comprising:
   a gas sensitive part;
   two detection electrodes electrically connected with each other through the gas sensitive part; and a protective layer enclosing the gas sensitive part and the detection electrodes, wherein the protective layer has an opening region, through which the gas sensitive part is exposed to an outside air, and the gas sensitive part is formed from an oxygen containing compound semiconductor material;

wherein when one of the detection electrodes is applied with a detecting signal, the detecting signal is output from the other detection electrode after being modulated by the gas sensitive part, and a voltage signal output by the other detection electrode is related to the nature of the outside air to which the gas sensitive part is exposed;

wherein the protective layer is formed above the gas sensitive part and the detection electrodes and contacts the gas sensitive part and the detection electrodes directly, the gas sensitive part is overlapped with the detection electrodes partly, and in the overlap region, the detection electrodes are between the gas sensitive part and the protective layer.

2. The gas detection sensor according to claim 1, further comprising a heating electrode electrically insulated from the gas sensitive part and configured to convert electrical energy to heat energy so as to heat the gas sensitive part.

3. The gas detection sensor according to claim 2, further comprising a heating electrode wire configured to be electrically connected with the heating electrode for providing electrical energy to the heating electrode.

4. The gas detection sensor according to claim 3, further comprising a connecting portion connected in parallel with the heating electrode wire and configured to decrease the resistance of the heating electrode wire.

5. The gas detection sensor according to claim 1, wherein the oxygen containing compound semiconductor material comprises any one of zinc nitrogen oxides (ZnON), indium tin zinc oxides (ITZO), zinc tin oxides (ZTO), zinc indium oxides (ZIO), indium gallium oxides (IGO), indium gallium zinc oxides (IGZO), aluminum zinc tin oxides (AZTO), or any combination thereof.

6. A display panel, comprising:
an array substrate;
an opposing substrate disposed opposite to the array substrate;
an adhesive frame hermetically connecting the array substrate and the opposing substrate; and
at least one gas detection sensor according to claim 1,
wherein the gas detection sensor is disposed on the array substrate and/or the opposing substrate and located outside the adhesive frame.

7. The display panel according to claim 6, wherein
when the gas detection sensor is disposed on the array substrate, the gas sensitive part of the gas detection sensor and an active layer of a thin film transistor in the array substrate are located in the same layer and formed from the same material.

8. The display panel according to claim 7, wherein
the detection electrodes of the gas detection sensor and source and drain electrodes of a thin film transistor in the array substrate are located in the same layer and formed from the same material.

9. The display panel according to claim 7, wherein
the gas detection sensor comprises a heating electrode, the heating electrode is located underneath the gas sensitive part, and the heating electrode is electrically insulated from the gas sensitive part and configured to convert electrical energy to heat energy so as to heat the gas sensitive part;

when a gate electrode of a thin film transistor in the array substrate is located underneath an active layer of the thin film transistor, the heating electrode and the gate electrode are located in the same layer and formed from the same material; or when source and drain electrodes of the thin film transistor in the array substrate are located underneath the active layer, the heating electrode and the source and drain electrodes are located in the same layer and formed from the same material.

10. The display panel according to claim 7, wherein
the gas detection sensor comprises a heating electrode, the heating electrode is located underneath the gas sensitive part, and the heating electrode is electrically insulated from the gas sensitive part and configured to convert electrical energy to heat energy so as to heat the gas sensitive part;

the detection electrode and source and drain electrodes of a thin film transistor in the array substrate are located in the same layer and formed from the same material; and a gate electrode of the thin film transistor in the array substrate is located underneath an active layer of thin film transistor in the array substrate, the heating electrode and the gate electrode are located in the same layer and formed from the same material.

11. The display panel according to claim 7, wherein
the gas detection sensor comprises a heating electrode, the heating electrode is located underneath the gas sensitive part, and the heating electrode is electrically insulated from the gas sensitive part and configured to convert electrical energy to heat energy so as to heat the gas sensitive part;

the detection electrodes of the gas detection sensor and a gate electrode of a thin film transistor in the array substrate are located in the same layer and formed from the same material; and source and drain electrodes of the thin film transistor in the array substrate are located underneath an active layer of thin film transistor in the array substrate, the heating electrode and the source and drain electrodes are located in the same layer and formed from the same material.

12. The display panel according to claim 9, wherein
the gas detection sensor further comprises a heating electrode wire electrically connected to the heating electrode for providing electrical energy to the heating electrode and a connecting portion connected in parallel with the heating electrode wire to reduce the resistance of the heating electrode wire;

when the gate electrode of the thin film transistor in the array substrate is located underneath the active layer, and the heating electrode and the gate electrode are located in the same layer and formed from the same material:
the heating electrode wire and the heating electrode of the gas detection sensor are located in the same layer and formed from the same material; and
the connecting portion and the source and drain electrodes of the thin film transistor are located in the same layer and formed from the same material, and the connecting portion is electrically connected to the heating electrode wire through a via hole.

13. The display panel according to claim 10, wherein
the gas detection sensor further comprises a heating electrode wire electrically connected to the heating electrode for providing electrical energy to the heating electrode and a connecting portion connected in parallel with the heating electrode wire for reducing the resistance of the heating electrode wire;
the heating electrode wire and the heating electrode of the gas detection sensor are located in the same layer and formed from the same material; and
the connecting portion and the source and drain electrodes of the thin film transistor are located in the same layer and formed from the same material, and the connecting portion is electrically connected to the heating electrode wire through a via hole.

* * * * *